United States Patent
Knudson et al.

(10) Patent No.: US 8,798,754 B2
(45) Date of Patent: Aug. 5, 2014

(54) NEURAL BLOCKING THERAPY

(75) Inventors: Mark B. Knudson, Shoreview, MN (US); Adrianus P. Donders, Andover, MN (US); Timothy R. Conrad, Eden Prairie, MN (US)

(73) Assignee: Venturi Group, LLC, St. Paul, MN (US)

( * ) Notice: Subject to any disclaimer, the term of this patent is extended or adjusted under 35 U.S.C. 154(b) by 1146 days.

(21) Appl. No.: 12/045,394

(22) Filed: Mar. 10, 2008

(65) Prior Publication Data

US 2008/0154333 A1 Jun. 26, 2008

Related U.S. Application Data

(62) Division of application No. 11/235,947, filed on Sep. 26, 2005.

(51) Int. Cl.
*A61N 1/36* (2006.01)

(52) U.S. Cl.
USPC .......................................................... 607/45

(58) Field of Classification Search
USPC ..................................................... 607/45–46
See application file for complete search history.

(56) References Cited

U.S. PATENT DOCUMENTS

| | | | |
|---|---|---|---|
| 1,597,061 A | 8/1926 | Cultra | |
| 2,622,601 A | 12/1952 | Nemec | |
| 3,646,940 A | 3/1972 | Timm et al. | |
| 3,817,254 A | 6/1974 | Maurer | |
| 3,822,708 A | 7/1974 | Zilber | |
| 3,893,463 A | 7/1975 | Williams | |
| 4,014,347 A | 3/1977 | Halleck et al. | |
| 4,023,574 A | 5/1977 | Nemec | |
| 4,055,190 A | 10/1977 | Tany et al. | |
| 4,315,503 A | 2/1982 | Ryaby et al. | |

(Continued)

FOREIGN PATENT DOCUMENTS

| | | |
|---|---|---|
| EP | 1181947 | 2/2002 |
| GB | 2499546 | 11/2008 |

(Continued)

OTHER PUBLICATIONS

Kilgore, el al., "Nerve conduction block utilising high-frequency alternating current", Medical & Biological Engineering and Computing, vol. 24, pp. 394-406 (2004).*

(Continued)

*Primary Examiner* — Eric D. Bertram
(74) *Attorney, Agent, or Firm* — Perkins Coie LLP

(57) ABSTRACT

A method and apparatus are disclosed for treating a variety of conditions include treating a disorder associated with neural activity near a region of a brain. In such condition, the method includes placing an electrode to create a field near said region, creating said field with parameters selected to at least partially block neural activity within said field. For treating a tissue sensation, the method includes identifying a target area of tissue to be treated and placing an electrode to create a field near the target area, and creating the field with parameters selected to at least partially block neural activity within the target area. For treating a condition associated with neural activity of a spinal cord, the method includes placing an electrode to create a field near a nerve associated with the spinal cord, and creating the field with parameters selected to at least partially block neural activity within the nerve.

23 Claims, 6 Drawing Sheets

(56) References Cited

U.S. PATENT DOCUMENTS

| | | | |
|---|---|---|---|
| 4,414,986 A | 11/1983 | Dickhudt et al. |
| 4,459,989 A | 7/1984 | Borkan |
| 4,535,777 A | 8/1985 | Castel |
| 4,541,432 A | 9/1985 | Molina-Negro et al. |
| 4,649,935 A | 3/1987 | Charmillot et al. |
| 4,702,254 A | 10/1987 | Zabara |
| 4,841,973 A | 6/1989 | Stecker |
| 5,002,053 A | 3/1991 | Garcia-Rill |
| 5,121,754 A | 6/1992 | Mullett |
| 5,188,104 A | 2/1993 | Wernicke et al. |
| 5,229,569 A | 7/1993 | Miyauchi et al. |
| 5,335,657 A | 8/1994 | Terry, Jr. et al. |
| 5,417,719 A | 5/1995 | Hull et al. |
| 5,501,703 A | 3/1996 | Holsheimer et al. |
| 5,514,175 A | 5/1996 | Kim et al. |
| 5,540,730 A | 7/1996 | Terry, Jr. et al. |
| 5,562,717 A | 10/1996 | Tippey et al. |
| 5,643,330 A | 7/1997 | Holsheimer et al. |
| 5,707,396 A * | 1/1998 | Benabid ............ 607/2 |
| 5,716,377 A | 2/1998 | Rise et al. |
| 5,733,322 A | 3/1998 | Starkebaum |
| 5,776,170 A | 7/1998 | MacDonald et al. |
| 5,792,187 A * | 8/1998 | Adams ............... 607/5 |
| 5,830,151 A | 11/1998 | Hadzic et al. |
| 5,853,373 A | 12/1998 | Griffith et al. |
| 5,893,883 A | 4/1999 | Torgerson |
| 5,895,416 A | 4/1999 | Barreras, Sr. et al. |
| 5,948,007 A | 9/1999 | Starkebaum et al. |
| 5,983,141 A | 11/1999 | Sluijter et al. |
| 5,995,872 A | 11/1999 | Bourgeois |
| 6,002,964 A | 12/1999 | Feler et al. |
| 6,014,588 A | 1/2000 | Fitz |
| 6,104,957 A | 8/2000 | Alo et al. |
| 6,161,044 A | 12/2000 | Silverstone |
| 6,167,305 A | 12/2000 | Cammilli et al. |
| 6,167,311 A | 12/2000 | Rezai |
| 6,176,242 B1 | 1/2001 | Rise |
| 6,233,488 B1 | 5/2001 | Hess |
| 6,238,423 B1 | 5/2001 | Bardy |
| 6,246,912 B1 | 6/2001 | Sluijter et al. |
| 6,341,236 B1 | 1/2002 | Osorio et al. |
| 6,356,786 B1 | 3/2002 | Rezai et al. |
| 6,381,496 B1 | 4/2002 | Meadows et al. |
| 6,405,079 B1 | 6/2002 | Ansarinia |
| 6,421,566 B1 | 7/2002 | Holsheimer |
| 6,438,423 B1 | 8/2002 | Rezai et al. |
| 6,440,090 B1 | 8/2002 | Schallhorn |
| 6,505,078 B1 | 1/2003 | King et al. |
| 6,510,347 B2 | 1/2003 | Borkan |
| 6,516,227 B1 | 2/2003 | Meadows et al. |
| 6,571,127 B1 | 5/2003 | Ben-Haim et al. |
| 6,584,358 B2 | 6/2003 | Carter et al. |
| 6,587,727 B2 | 7/2003 | Osorio et al. |
| 6,600,954 B2 | 7/2003 | Cohen et al. |
| 6,609,030 B1 | 8/2003 | Rezai et al. |
| 6,609,031 B1 | 8/2003 | Law et al. |
| 6,610,713 B2 | 8/2003 | Tracey |
| 6,622,047 B2 | 9/2003 | Barrett et al. |
| 6,622,048 B1 | 9/2003 | Mann |
| 6,671,556 B2 | 12/2003 | Osorio et al. |
| 6,675,046 B2 | 1/2004 | Holsheimer |
| 6,684,105 B2 | 1/2004 | Cohen et al. |
| 6,871,090 B1 | 3/2005 | He et al. |
| 6,885,888 B2 | 4/2005 | Rezai |
| 6,895,280 B2 | 5/2005 | Meadows et al. |
| 6,907,295 B2 | 6/2005 | Gross et al. |
| 6,920,357 B2 | 7/2005 | Osorio et al. |
| 6,928,320 B2 | 8/2005 | King |
| 6,968,237 B2 | 11/2005 | Doan et al. |
| 7,024,246 B2 | 4/2006 | Acosta et al. |
| 7,047,079 B2 | 5/2006 | Erickson |
| 7,082,333 B1 | 7/2006 | Bauhahn et al. |
| 7,117,034 B2 | 10/2006 | Kronberg |
| 7,162,303 B2 * | 1/2007 | Levin et al. .......... 607/44 |
| 7,177,690 B2 | 2/2007 | Woods et al. |
| 7,177,691 B2 | 2/2007 | Meadows et al. |
| 7,180,760 B2 | 2/2007 | Varrichio et al. |
| 7,212,865 B2 | 5/2007 | Cory |
| 7,236,822 B2 | 6/2007 | Dobak, III |
| 7,239,912 B2 | 7/2007 | Dobak, III |
| 7,252,090 B2 | 8/2007 | Goetz |
| 7,260,436 B2 | 8/2007 | Kilgore et al. |
| 7,266,412 B2 | 9/2007 | Stypulkowski |
| 7,276,057 B2 | 10/2007 | Gerber |
| 7,313,440 B2 | 12/2007 | Miesel |
| 7,324,852 B2 | 1/2008 | Barolat et al. |
| 7,326,181 B2 | 2/2008 | Katims |
| 7,333,857 B2 | 2/2008 | Campbell |
| 7,337,005 B2 | 2/2008 | Kim et al. |
| 7,337,006 B2 | 2/2008 | Kim et al. |
| 7,349,743 B2 | 3/2008 | Tadlock |
| 7,389,145 B2 | 6/2008 | Kilgore et al. |
| 7,393,351 B2 | 7/2008 | Woloszko et al. |
| 7,493,172 B2 | 2/2009 | Whitehurst et al. |
| 7,502,651 B2 | 3/2009 | Kim et al. |
| 7,502,652 B2 | 3/2009 | Gaunt et al. |
| 7,689,289 B2 | 3/2010 | King |
| 7,734,340 B2 | 6/2010 | De Ridder |
| 7,742,810 B2 | 6/2010 | Moffitt et al. |
| 7,761,170 B2 | 7/2010 | Kaplan et al. |
| 7,813,803 B2 | 10/2010 | Heruth et al. |
| 7,826,901 B2 | 11/2010 | Lee et al. |
| 7,860,570 B2 | 12/2010 | Whitehurst et al. |
| 7,877,136 B1 | 1/2011 | Moffitt et al. |
| 7,890,176 B2 | 2/2011 | Jaax et al. |
| 8,170,675 B2 | 5/2012 | Alataris et al. |
| 8,209,021 B2 | 6/2012 | Alataris et al. |
| 8,209,028 B2 | 6/2012 | Skelton et al. |
| 8,224,453 B2 | 7/2012 | De Ridder |
| 8,280,515 B2 | 10/2012 | Greenspan |
| 8,355,792 B2 | 1/2013 | Alataris et al. |
| 8,359,102 B2 | 1/2013 | Alataris et al. |
| 8,359,103 B2 | 1/2013 | Alataris et al. |
| 8,380,318 B2 | 2/2013 | Kishawi et al. |
| 8,396,559 B2 | 3/2013 | Alataris et al. |
| 8,423,147 B2 | 4/2013 | Alataris et al. |
| 8,509,905 B2 | 8/2013 | Alataris et al. |
| 2002/0055779 A1 | 5/2002 | Andrews |
| 2002/0116030 A1 | 8/2002 | Rezai |
| 2002/0128700 A1 | 9/2002 | Cross |
| 2003/0018368 A1 | 1/2003 | Ansarinia |
| 2003/0120323 A1 | 6/2003 | Meadows et al. |
| 2003/0125786 A1 | 7/2003 | Gliner et al. |
| 2003/0144709 A1 | 7/2003 | Zabara et al. |
| 2003/0195602 A1 | 10/2003 | Boling |
| 2004/0015202 A1 | 1/2004 | Chandler et al. |
| 2004/0034394 A1 | 2/2004 | Woods et al. |
| 2004/0039425 A1 | 2/2004 | Greenwood-Van Meerveld |
| 2004/0044379 A1 | 3/2004 | Holsheimer |
| 2004/0073273 A1 * | 4/2004 | Gluckman et al. .......... 607/48 |
| 2004/0093093 A1 | 5/2004 | Andrews |
| 2004/0127942 A1 | 7/2004 | Yomtov et al. |
| 2004/0127953 A1 | 7/2004 | Kilgore et al. |
| 2004/0138721 A1 | 7/2004 | Osorio et al. |
| 2004/0162590 A1 | 8/2004 | Whitehurst et al. |
| 2004/0167583 A1 | 8/2004 | Knudson et al. |
| 2004/0167584 A1 | 8/2004 | Carroll et al. |
| 2004/0172085 A1 | 9/2004 | Knudson et al. |
| 2004/0172086 A1 | 9/2004 | Knudson et al. |
| 2004/0172088 A1 | 9/2004 | Knudson et al. |
| 2004/0176812 A1 | 9/2004 | Knudson et al. |
| 2004/0210270 A1 | 10/2004 | Erickson |
| 2004/0243205 A1 | 12/2004 | Keravel et al. |
| 2004/0249416 A1 | 12/2004 | Yun et al. |
| 2005/0021092 A1 | 1/2005 | Yun et al. |
| 2005/0033376 A1 | 2/2005 | Whitehurst |
| 2005/0033381 A1 | 2/2005 | Carter et al. |
| 2005/0038484 A1 | 2/2005 | Knudson et al. |
| 2005/0038489 A1 | 2/2005 | Grill |
| 2005/0038490 A1 | 2/2005 | Gross et al. |
| 2005/0060001 A1 | 3/2005 | Singhal et al. |
| 2005/0065394 A1 | 3/2005 | Spiegel |
| 2005/0065562 A1 | 3/2005 | Rezai |
| 2005/0065573 A1 | 3/2005 | Rezai |

(56) References Cited

U.S. PATENT DOCUMENTS

| | | |
|---|---|---|
| 2005/0107841 A1 | 5/2005 | Meadows et al. |
| 2005/0113882 A1 | 5/2005 | Cameron et al. |
| 2005/0119703 A1 | 6/2005 | DiLorenzo |
| 2005/0119713 A1 | 6/2005 | Whitehurst et al. |
| 2005/0143788 A1 | 6/2005 | Yun et al. |
| 2005/0143789 A1 | 6/2005 | Whitehurst et al. |
| 2005/0149148 A1 | 7/2005 | King |
| 2005/0153885 A1 | 7/2005 | Yun et al. |
| 2005/0182453 A1 | 8/2005 | Whitehurst et al. |
| 2005/0240242 A1 | 10/2005 | DiLorenzo |
| 2005/0267545 A1 | 12/2005 | Cory |
| 2006/0004422 A1 | 1/2006 | De Ridder |
| 2006/0030895 A1 | 2/2006 | Simon et al. |
| 2006/0041285 A1 | 2/2006 | Johnson |
| 2006/0052826 A1 | 3/2006 | Kim et al. |
| 2006/0052835 A1 | 3/2006 | Kim et al. |
| 2006/0074456 A1 | 4/2006 | Pyles et al. |
| 2006/0095088 A1 | 5/2006 | De Ridder |
| 2006/0100671 A1 | 5/2006 | Ridder |
| 2006/0116742 A1 | 6/2006 | De Ridder |
| 2006/0161219 A1 | 7/2006 | Mock et al. |
| 2006/0161235 A1 | 7/2006 | King |
| 2006/0190048 A1 | 8/2006 | Gerber |
| 2006/0229687 A1 | 10/2006 | Goetz et al. |
| 2007/0021801 A1 | 1/2007 | Heruth et al. |
| 2007/0021802 A1 | 1/2007 | Heruth et al. |
| 2007/0021803 A1 | 1/2007 | Deem et al. |
| 2007/0032827 A1 | 2/2007 | Katims |
| 2007/0039625 A1 | 2/2007 | Heruth et al. |
| 2007/0049991 A1 | 3/2007 | Klostermann et al. |
| 2007/0060954 A1 | 3/2007 | Cameron et al. |
| 2007/0073353 A1 | 3/2007 | Rooney et al. |
| 2007/0073354 A1 | 3/2007 | Knudson et al. |
| 2007/0142863 A1 | 6/2007 | Bradley |
| 2007/0150034 A1 | 6/2007 | Rooney et al. |
| 2007/0179559 A1 | 8/2007 | Giftakis et al. |
| 2007/0179579 A1 | 8/2007 | Feler et al. |
| 2007/0213771 A1 | 9/2007 | Spinner et al. |
| 2007/0239226 A1 | 10/2007 | Overstreet |
| 2007/0244522 A1 | 10/2007 | Overstreet |
| 2007/0293915 A1 | 12/2007 | Kilgore et al. |
| 2007/0299482 A1 | 12/2007 | Littlewood et al. |
| 2008/0015667 A1 | 1/2008 | Gross |
| 2008/0033511 A1 | 2/2008 | Dobak |
| 2008/0058878 A1 | 3/2008 | King |
| 2008/0058888 A1 | 3/2008 | King |
| 2008/0103570 A1 | 5/2008 | Gerber |
| 2008/0109045 A1 | 5/2008 | Gross et al. |
| 2008/0167697 A1 | 7/2008 | Johnson |
| 2008/0183259 A1 | 7/2008 | Bly et al. |
| 2008/0234791 A1 | 9/2008 | Arle et al. |
| 2008/0294221 A1 | 11/2008 | Kilgore et al. |
| 2009/0036945 A1 | 2/2009 | Chancellor et al. |
| 2009/0054962 A1 | 2/2009 | Lefler et al. |
| 2009/0132010 A1 | 5/2009 | Kronberg |
| 2009/0157141 A1 | 6/2009 | Chiao et al. |
| 2009/0157149 A1 | 6/2009 | Wahlgren et al. |
| 2009/0198306 A1 | 8/2009 | Goetz et al. |
| 2009/0204173 A1 | 8/2009 | Fang et al. |
| 2009/0204192 A1 | 8/2009 | Carlton et al. |
| 2009/0210041 A1 | 8/2009 | Kim et al. |
| 2009/0281595 A1 | 11/2009 | King et al. |
| 2009/0287274 A1 | 11/2009 | De Ridder |
| 2009/0326115 A1 | 12/2009 | Gillbe |
| 2010/0016929 A1 | 1/2010 | Prochazka |
| 2010/0036454 A1 | 2/2010 | Bennett et al. |
| 2010/0094375 A1 | 4/2010 | Donders et al. |
| 2010/0125313 A1 | 5/2010 | Lee et al. |
| 2010/0137938 A1 | 6/2010 | Kishawi et al. |
| 2010/0191307 A1 | 7/2010 | Fang et al. |
| 2010/0228325 A1 | 9/2010 | Moffitt et al. |
| 2010/0241190 A1 | 9/2010 | Kilgore et al. |
| 2010/0274312 A1 | 10/2010 | Alataris et al. |
| 2010/0274314 A1 | 10/2010 | Alataris et al. |
| 2010/0274315 A1 | 10/2010 | Alataris et al. |
| 2010/0274316 A1 | 10/2010 | Alataris et al. |
| 2010/0274317 A1 | 10/2010 | Parker et al. |
| 2010/0274318 A1 | 10/2010 | Walker et al. |
| 2010/0274320 A1 | 10/2010 | Torgerson |
| 2010/0274326 A1 | 10/2010 | Chitre |
| 2010/0324630 A1 | 12/2010 | Lee et al. |
| 2011/0009919 A1 | 1/2011 | Carbunaru et al. |
| 2011/0009923 A1 | 1/2011 | Lee |
| 2011/0022114 A1 | 1/2011 | Navarro |
| 2011/0184486 A1 | 7/2011 | De Ridder |
| 2011/0282412 A1 | 11/2011 | Glukhovsky et al. |
| 2012/0089200 A1 | 4/2012 | Ranu et al. |
| 2012/0277833 A1 | 11/2012 | Gerber et al. |
| 2012/0283797 A1 | 11/2012 | De Ridder |
| 2013/0006325 A1 | 1/2013 | Woods et al. |
| 2013/0023951 A1 | 1/2013 | Greenspan |
| 2013/0066411 A1 | 3/2013 | Thacker et al. |
| 2013/0096643 A1 | 4/2013 | Fang et al. |
| 2013/0096644 A1 | 4/2013 | Fang et al. |
| 2013/0110196 A1 | 5/2013 | Alataris et al. |
| 2013/0123879 A1 | 5/2013 | Alataris et al. |
| 2013/0204173 A1 | 8/2013 | Kelly et al. |
| 2013/0204320 A1 | 8/2013 | Alataris et al. |
| 2013/0204321 A1 | 8/2013 | Alataris et al. |
| 2013/0204322 A1 | 8/2013 | Alataris et al. |
| 2013/0204323 A1 | 8/2013 | Thacker et al. |
| 2013/0204324 A1 | 8/2013 | Thacker et al. |
| 2013/0204338 A1 | 8/2013 | Alataris et al. |
| 2013/0211487 A1 | 8/2013 | Fang et al. |
| 2013/0261695 A1 | 10/2013 | Thacker et al. |
| 2013/0261696 A1 | 10/2013 | Thacker et al. |
| 2013/0261697 A1 | 10/2013 | Thacker et al. |
| 2014/0031896 A1 | 1/2014 | Alataris et al. |

FOREIGN PATENT DOCUMENTS

| | | |
|---|---|---|
| JP | 2007528774 A | 10/2007 |
| WO | WO-02065896 A2 | 8/2002 |
| WO | WO-02092165 A1 | 11/2002 |
| WO | WO-2007082382 A1 | 7/2007 |
| WO | WO-2007117232 A1 | 10/2007 |
| WO | WO-2008039982 A2 | 4/2008 |
| WO | WO-2008045434 A2 | 4/2008 |
| WO | WO-2008106174 A1 | 9/2008 |
| WO | WO-2008121891 A1 | 10/2008 |
| WO | WO-2008153726 A2 | 12/2008 |
| WO | WO-2009018518 A1 | 2/2009 |
| WO | WO-2011014570 A1 | 2/2011 |

OTHER PUBLICATIONS

Office Action mailed May 10, 2007 from parent U.S. Appl. No. 11/235,947.

Final Office Action mailed Feb. 28, 2008 from parent U.S. Appl. No. 11/235,947.

Dapoigny et al., "Vagal influence on colonic motor activity in conscious nonhuman primates", *Am. J. Physiol.*, 262: G231-G236 (1992).

Grill, W. et al., "Stimulus Waveforms for Selective Neural Stimulation," *IEEE Engineering in Medicine and Biology*, pp. 375-385 (Jul./Aug. 1995).

Holsheimer, J., "Effectiveness of Spinal Cord Stimulation in the Management of Chronic Pain: Analysis of Technical Drawbacks and Solutions," *Neurosurgery*, vol. 40, No. 5, pp. 990-999 (May 1997).

Kilgore, et al., "Nerve conduction block utilizing high-frequency alternating current", *Medical & Biological Engineering and Computing*, vol. 24, pp. 394-406 (2004).

Paterson CA, et al., "Determinants of Occurrence and Volume of Transpyloric Flow During Gastric Emptying of Liquids in Dogs: Importance of Vagal Input", *Dig Dis Sci*, (2000);45:1509-1516.

Petrofsky, et al., "Impact of Recruitment Order on Electrode Design for Neural Prosthetics of Skeletal Muscle", *Am. J. of Physical Medicine*, vol. 60, No. 5, pp. 243-253 (1981).

Solomonow, et al., "Control of Muscle Contractile Force Through Indirect High-Frequency Stimulation", *Am. J. of Physical Medicine*, vol. 62, No. 2, pp. 71-82 (1983).

(56) References Cited

OTHER PUBLICATIONS

Van Den Honert, et al., "Generation of Unidirectionally Propagated Action Potentials in a Peripheral Nerve by Brief Stimuli", *Science*, vol. 206, pp. 1311-1312.
Capdevila et al., "Continuous Peripheral Nerve Blocks in Hospital Wards after Orthopedics Surgery," Anesthesiology 2005, 103:1035-45, 10 pages.
Bowman and McNeal, Response of Single Alpha Motoneurons to High-Frequency Pulse Trains, Appl. Neurophysiol. 49, p. 121-138, 1986, 10 pages.
Hopp et al., "Effect of anodel blockade of myelinated fibers on vagal c-fiber afferents," Am J. Physiol. Nov. 1980; 239(5), 9 pages.
Huxely et al., "Excitation and Conduction in Nerve: Quantitative Analysis," Science, Sep. 11, 1964; 145: 1154-9.
Van Den Honert, Mortimer JT, "A Technique for Collision Block of Peripheral Nerve: Frequency Dependence," MP-11 IEEE Trans. Biomed, Eng. 28: 379-382, 1981.
Woo MY, Campbell B. "Asynchronous Firing and Block of Peripheral Nerve Conduction by 20KC Alternating Current," Los Angeles Neuro Society, Jun. 1964; 87-94. 5 pages.
Bhadra MD, Niloy et al., "High-Frequency Electrical Conduction Block of Mammalian Peripheral Motor Nerve," Muscle and Nerve, Dec. 2005, 9 pages.
Jang et al., "Analysis of Failed Spinal Cord Stimulation Trails in the Treatment of Intractable Chronic Pain," J. Korean Neurosurg Soc 43, 2008, 5 pages.
Linderoth et al., "Mechanisms of Spinal Cord Stimulation in Painful Syndromes: Role of Animal Models," Pain Medicine, vol. 7, No. S1, 2006, 13 pages.
Linderoth et al., "Physiology of Spinal Cord Stimulation: Review and Update," Neuromodulation, vol. 2, No. 3, 1999, 15 pages.
Mediati, R.D., , Mechanisms of Spinal Cord Stimulation, Florence Oct. 2, 2002.
Melzack, Ronald et al., "Pain Mechanisms: A New Theory," Science, vol. 150, No. 3699, Nov. 19, 1965, 9 pages.
Oakley, John C., "Spinal Cord Stimulation Mechanisms of Action," SPINE vol. 27, No. 22, copyright 2002, 10 pages.
Shealy MD, C. Norman et al., "Electrical Inhibition of Pain by Stimulation of the Dorsal Columns: Preliminary Clinical Report," Anesthesia and Analgesia . . . Current Researches, vol. 446, No. 4, Jul.-Aug. 1967,3 pages.
Vadalouca et al., "Therapeutic Management of Chronic Neuropathic Pain: An Examination of Pharmacologic Treatment," Annals New York Academy of Sciences, 2006, pp. 164-186.
Zhang et al., "Simulation Analysis of Conduction Block in Myelinated Axons Induced by High-Frequency Biphasic Rectangular Pulses," IEEE Transactions on Biomedical Engineering, vol. 53., No. 7, Jul. 2006, 4 pages.
Alo et al., "New Trends in Neuromodulation for the Management of Neuropathic Pain," Neurosurgery, vol. 50, No. 4, Apr. 2002, 15 pages.
Bahdra et al., Stimulation of High-Frequency Sinusoidal Electrical Block of Mammalian Myelinated Axons, J Comput Neurosco, 22:313-326, 2007.
Barolat et al., "Multifactorial Analysis of Epidural Spinal Cord Stimulation," Sterotactic and Functional Neurosurgery, 1991; 56: 77-103.
Bhadra et al., "High Frequency electrical conduction block of the pudendal nerve," Journal of Neural Engineering—Institute of Physics Publishing, 2006, 8 pages.
Boger et al., "Bladder Voiding by Combined High Frequency Electrical Pudendal Nerve Block and Sacral Root Stimulation," Neurourology and Urodynamics, 27, 2008, 5 pages.
Burton, Charles, "Dorsal Column Stimulation: Optimization of Application," Surgical Neurology, vol. 4, No. 1, Jul. 1975, 10 pages.
Cuellar et al., "Effect of High Frequency Alternating Current on Spinal Afferent Nociceptive Transmission," Neuromodulation: Technology at the Neural Interface, 2012, 10 pages.
DeRidder et al., "Are Paresthesias necessary for pain suppression in SCS—Burst Stimulation," Brain, Brain Research Center Antwerp of Innovative and Interdisciplinary Neuromodulation, 2010, 27 pages.
DeRidder et al., "Burst Spinal Cord Stimulation: Toward Paresthesia-Free Pain Suppression," www.neurosurgery-online.com, vol. 66, Nos. 5, May 2010, 5 pages.
Holsheimer—Effectiveness of Spinal Cord Stimulation in the Management of Chronic Pain: Analysis of Technicall Drawbacks and Solutions, Neurosurgery, vol. 40, No. 5, May 1997, pp. 990-999.
Hoppenstein, Reuben, "Electrical Stimulation of the Ventral and Dorsal Columns of the Spinal Cord for Relief of Chronic Intractable Pain: Preliminary Report," Surgical Neurology, vol. 4, No. 1, Jul. 1975, 9 pages.
Kilgore et al. "Reversible Nerve Conduction Block Using Kilohertz Frequency Alternating Current," Neuromodulation Technology at the Neural Interface, International Neuromodulation Society, 2013, 13 pages.
Kumar et al., "Spinal Cord Stimulation in Treatment of Chronic Benign Pain: Challenges in Treatment Planning and Present Status, a 22-Year Experience," Neurosurgery, vol. 58, No. 3, Mar. 2006, 16 pages.
North et al., "Failed Back Surgery Syndrome: 5-year Follow-Up after Spinal Cord Stimulator Implantation," Neurosurgery, Official Journal of the Congress of Neurological Surgeons, vol. 28, No. 5, May 1991, 9 pages.
North et al., "Spinal Cord Stimulation for Axial Low Back Pain," SPINE, vol. 30, No. 12, 2005, 7 pages.
North et al., "Spinal Cord Stimulation for Chronic, Intractable Pain: Experience over Two Decades," Neurosurgery, vol. 32, No. 2, Mar. 1993, 12 pages.
Perruchoud et al., "Analgesic Efficacy of High-Frequency Spinal Cord Stimulation: A Randomized Double-Blind Placebo-Controlled Study," Neuromodulation: Technology at Neural Interface, International Neuromodulation Society, 2013, 7 pages.
Simpson, BA, "Spinal Cord Stimulation in 60 cases of Intractable Pain." Journal of Neurology, Neurosurgery and Psychiatry, 1991; 54 pages 196-199.
Tiede et al., "Novel Spinal Cord Stimulation Parameters in Patients with Predominate Back Pain," Neuromodulation: Technology at the Neural Interface, 2013, 6 pages.
Urban et al., "Percutaneous epidural stimulation of the spinal cord for relief of pain—Long Term Results," Journal of Neurosurgery, vol. 48, Mar. 1978, 7 pages.
Van Butyen et al., "High Frequency Spinal Cord Stimulation for the Treatment of Chronic Back Pain Patients: Results of a Prospective; Multicenter European Clinical Study," Neuromodulation Technology at the Neural Interface, International Neuromodulation Society, 2012, 8 pages.
Wolter et al., "Continuous Versus Intermittent Spinal Cord Stimulation: An Analysis of Factors Influencing Clinical Efficacy," Neuromodulation: Technology at Neural Interface, www.neuromodulationjournal.com, 2011, 8 pages.

\* cited by examiner

NEURAL BLOCKING THERAPY

CROSS REFERENCE TO RELATED APPLICATIONS

This application is a divisional of application Ser. No. 11/235,947, filed Sep. 26, 2005, which application is incorporated herein by reference.

BACKGROUND OF THE INVENTION

1. Field of the Invention

This application pertains to method and apparatus for treating conditions associated with neuronal activity.

2. Description of the Prior Art a. Neural Stimulation Treatments

The prior art contains numerous examples of treatments involving stimulation signals to nerves, muscles or organs for treating a wide variety of medical disorders.

U.S. Pat. Nos. 4,702,254 and 5,229,569 (both assigned to Cyberonics, Inc.) describe various central nervous system (CNS) treatments using electrical stimulation applied to the vagus nerve. For example, the '254 patent describes treatment of epilepsy. The '569 patent describes treatment of neuropsychiatric disorders. U.S. patent application Publ. No. 2003/0144709 (also assigned to Cyberonics, Inc.) describes treatment of pain through nerve stimulation.

U.S. patent application publication No. 2004/0243205 A1 to Keravel et al. published Dec. 2, 2004 and assigned to Medtronic, Inc., Minneapolis, Minn., USA (incorporated herein by reference) describes a paddle lead with multiple electrodes. The paddle is placed beneath the skull overlying a target area of the cerebral cortex. The electrodes record somaestheic-evoked potentials. The same electrodes may be used for a stimulation therapy.

Nerve stimulation and muscle stimulation have been suggested for treating gastro-intestinal (GI) disorders. Treatments of gastrointestinal diseases through nerve stimulation have been suggested. For example, U.S. Pat. No. 6,238,423 to Bardy dated May 29, 2001 describes a constipation treatment involving electrical stimulation of the muscles or related nerves of the gut. U.S. Pat. No. 6,571,127 to Ben-Haim et al. dated May 27, 2003 describes increasing motility by applying an electrical field to the GI tract. U.S. Pat. No. 5,540,730 to Terry, Jr. et al., dated Jul. 30, 1996 describes a motility treatment involving vagal stimulation to alter GI contractions in response to a sense condition indicative of need for treatment. U.S. Pat. No. 6,610,713 to Tracey dated Aug. 26, 2003 describes inhibiting release of a proinflammatory cytokine by treating a cell with a cholinergic agonist by stimulating efferent vagus nerve activity to inhibit the inflammatory cytokine cascade. U.S. Pat. No. 6,622,047 to Barret et al dated Sep. 16, 2003 described obesity treatment through vagal stimulation.

b. Neural Blocking

The fore-going treatments are stimulation for treatments. For those applying a signal to a nerve, the signal parameters (pulse width, frequency and amplitude) are selected to initiate neural action potentials to be propagated along the nerve to an organ (e.g., brain or stomach).

Not all electrical signals applied to nerves are stimulation signals. Certain parameters can result in a signal that inhibits the nerve or blocks the propagation of action potentials along the nerve.

Many different forms of nerve blocking are known. The present invention is an improvement upon a neural blocking to avoid antidromic influences during stimulation or to otherwise down-regulate nerve activity. Cryogenic nerve blocking of the vagus is described in Dapoigny et al., "Vagal influence on colonic motor activity in conscious nonhuman primates", *Am. J. Physiol.*, 262: G231-G236 (1992). Electrically induced nerve blocking is described in Van Den Honert, et al., "Generation of Unidirectionally Propagated Action Potentials in a Peripheral Nerve by Brief Stimuli", *Science*, Vol. 206, pp. 1311-1312. An electrical nerve block is described in Solomonow, et al., "Control of Muscle Contractile Force through Indirect High-Frequency Stimulation", *Am. J. of Physical Medicine*, Vol. 62, No. 2, pp. 71-82 (1983) and Petrofsky, et al., "Impact of Recruitment Order on Electrode Design for Neural Prosthetics of Skeletal Muscle", *Am. J. of Physical Medicine*, Vol. 60, No. 5, pp. 243-253 (1981). A neural prosthesis with an electrical nerve block is also described in U.S. Patent Application Publication No. US 2002/0055779 A1 to Andrews published May 9, 2002. A cryogenic vagal block and resulting effect on gastric emptying are described in Paterson C A, et al., "Determinants of Occurrence and Volume of Transpyloric Flow During Gastric Emptying of Liquids in Dogs: Importance of Vagal Input", *Dig Dis Sci*, (2000); 45:1509-1516.

A frequency of the blocking signal is greater than a 200 Hz threshold and, preferably, greater than 500 Hz. Solomonow, et al. "control of muscle contractile force through indirect high-frequency stimulation", American Journal of Physical Medicine, Volume 62, No. 2, pages 71-82 (1983). Higher frequencies of as high as 5,000 Hz result in more consistent neural conduction block. Kilgore, et al., "Nerve Conduction Block Utilizing High-Frequency Alternating Current", *Medical and Biological Engineering and Computing*, Vol. 24, pp. 394-406 (2004).

The nerve conduction block is applied with electrical signals selected to block the entire cross-section of the nerve (for example, both afferent, efferent, myelinated and non-myelinated fibers) at the site of applying the blocking signal (as opposed to selected sub-groups of nerve fibers or just afferent and not efferent or vice versa).

c. Use of Neural Blocking in Treatments

U.S. Pat. No. 5,188,104 to Wernicke et. al. Dated Feb. 23, 1993 describes sub-selection of fibers in a nerve by selecting a treatment frequency by which blocks certain nerve fiber types in the nerve while stimulating other nerve fiber types. Since certain fibers are stimulated while other fibers are blocked, there is no cross-section inhibition or blocking of the entire nerve and all of its nerve fiber types (for example, both afferent, efferent, myelinated and non-myelinated fibers).

U.S. Pat. No. 6,684,105 to Cohen et al. dated Jan. 27, 2004 (assigned to Biocontrol Medical Ltd.) teaches collision blocking in which a stimulation signal is applied to a nerves and an appropriately timed stimulus is applied to nerve to create neural impulses which collide with and thereby block propagation of the stimulation signal in a given direction. No therapy is achieved by the blocking. Such blocking avoids adverse side effects associated with permitting the stimulation signal propagating in an undesired direction to an organ not targeted for therapy.

U.S. patent application Publ. No. 2002/0055779 A1 published May 9, 2002 describes applying a high frequency block to a sciatic nerve to block undesired neural impulses which would otherwise contribute to spastic movement. With such spasm-inducing signals blocked, a therapy signal is applied to the muscle to stimulated desired muscle contractions. U.S. patent application Publ. No. 2005/0149148 A1 published Jul. 7, 29005 (assigned to Medtronic, Inc.) teaches using a blocking signal to avoid undesired side effect (i.e., pain) otherwise associated with a stimulation signal.

The use of a blocking signal as a therapy is described in various patent applications assigned to EnteroMedics, Inc. These applications pertain to use of a conduction block technology to a nerve for a treatment of a variety of disorders. These applications include the following (all filed Sep. 29, 2003): U.S. patent application Ser. No. 10/674,330 (published Sep. 2, 2004 as Publication No. US 2004/0172086 A1); U.S. patent application Ser. No. 10/675,818 (published Sep. 9, 2004 as US Patent Application Publication No. US 2004/0176812 A1) and U.S. patent application Ser. No. 10/674,324 (published Sep. 2, 2004 as US Patent Application Publication No. 2004/0172085 A1). The same assignee is assigned U.S. patent application Ser. Nos. 10/752,994 and 10/752,940 both filed Jan. 6, 2004 with respective publication dates of Aug. 26, 2004 and Sep. 2, 2004, Publication Nos. US 2004/0167583 A1 and 2004/0172088 A1.

The foregoing EnteroMedics patent applications describe, in a preferred embodiment, the application of neural conduction block therapy to a vagus nerve alone or in combination with a stimulation of the nerve. The conduction block therapy of the these patent applications includes application of an electrical signal with parameters selected to down-regulate vagal activity by creating conditions in which normal nerve propagation potentials are blocked at the application of the signal on both afferent and efferent nerves fibers of the vagus. Representative treatments described in these applications include the treatment of obesity, pancreatitis, pain, inflammation, functional GI disorders, irritable bowel syndrome and ileus.

d. Accommodation

Blockage of a nerve can result in nerve accommodation in which other nerve groups assume, in whole in part, the function of the blocked nerve. For example, sub-diaphragm blocking of the vagus nerve may be accommodated by the enteric nervous system. U.S. patent application Ser. No. 10/881,045 filed Jun. 30, 2004 (published Feb. 17, 2005 as Publication No. US 2005/0038484 A1) (assigned to EnteroMedics, Inc.) notes that a duty cycle of electrical impulses to the nerve to block neural conduction on the nerve can be adjusted between periods of blocking and no blocking in order to vary the amount of down regulation of the vagus nerve as well as preventing accommodation by the enteric nervous system.

e. Drug Treatments

Many symptoms of Parkinson's disease can be controlled with one of many currently available medications. These are divided into several classes of drugs including dopamine agonists, levodopa/decarboxylase inhibitors, anticholinergic agents, MAO-B inhibitors, and COMT (catechol-O-methyltransferase) inhibitors. These medications, whether used alone or in combination, not only replace the dopamine that has been lost in the brain, but also slow the rate of dopamine loss in the brain, and/or correct the imbalance between the levels of dopamine and acetylcholine in the brain. While none of these medications are a cure for Parkinson's disease, they can alleviate the symptoms of the disease and help its victims manage the disease.

One of the most effective and widely administered medications introduced in the 1970's to relieve symptoms of Parkinson's disease works as a dopamine replacement therapy. This drug is known as Sinemet (generic name of levodopa/carbidopa), its active ingredient being L-DOPA (L-3,4-dihydroxyphenylanine). Levodopa is a generic name given to L-DOPA when it is produced as a drug. Unfortunately, dopamine cannot be administered directly to patients because it does not cross the blood-brain barrier. Hence, L-DOPA, which is the precursor form of dopamine, crosses the blood-brain barrier, and can be converted to dopamine in the brain, is the molecule of choice. However, due to the presence of aromatic amino acid decarboxylase (AADS) in the periphery of the brain, which will convert L-DOPA to dopamine before it crosses the blood brain barrier and prevent its passage to the brain, L-DOPA is administered with carbidopa, an AADS inhibitor. Carbidopa inhibits peripheral AADS action and thus reduces the amount of levodopa needed.

During the first few months the medication is administered, its benefits are maximal. However, patients taking Sinemet for a longer period are prone to the "wearing-off" effect, a tendency for the effectiveness of the drug to be lost with time. Hence, the dose of Sinemet will often have to be increased with time. Sometimes an "on-off effect," where the symptoms become sporadic and unpredictable over a period of time, is also experienced. Moreover, as the dose of the medication is increased, some patients begin to experience side effects due an increase in brain dopamine levels. Some major side effects include anxiety, agitation, dyskinesia, vomiting, low blood pressure, hallucination and nausea (Nadeau 1997). The occurrence of side effects limits the further increase in Sinemet's dosage and at this point, treatment options become limited. Fortunately, carbidopa minimizes the incidence of vomiting and nausea. Furthermore, although levodopa/carbidopa treatment decreases bradykinesia and rigidity, it may not relieve tremor and balance.

Sinemet (unlike most medications that are absorbed into blood through the stomach) is absorbed from the small intestine. Anything that delays the movement of food from the stomach to the small intestine, such as foods rich in fat and protein, can reduce the amount of the drug absorbed. Moreover, levodopa has a very short plasma half-life. It disappears from the blood in 60 to 90 minutes. Because it is a type of amino acid called a large neutral amino acid (LNAA), it attaches itself during absorption to carrier molecules in the wall of the intestine and is then carried to the blood. Similarly, once in the blood, carrier molecules carry it across the blood-brain barrier. Amino acids such as isoleucine, leucine, valine, phenylalanine, tryptophan and tyrosine compete for the carrier with levodopa. Hence, a diet rich in protein can further compete with the Sinemet for entry into the brain. Thus, it is important to carefully evaluate one's diet when taking Sinemet.

Another medication that can be used alone or in combination with Sinemet is Eldepryl (generic name of selegeline). Selegeline is classified as a MAO-B inhibitor and is often administered in 5 mg capsules to help keep the Sinemet dose lower over time and therefore extend its administration period. In certain cases, it can delay the need for levodopa therapy by up to a year. By blocking the action of MAO-B, selegeline extends the capabilities of the dopamine in the synapse, delaying the breakdown of naturally occurring dopamine and dopamine administered as L-DOPA. Eldepryl thus slows dopamine loss in the synapse and makes it more likely that a dopamine will reach its corresponding receptor on the receiving nerve cell and transmit the correct message down the dopamine circuit. This is often referred to as dopamine conservation therapy.

During the Fourth International Congress of Movement Disorders held in Vienna during the summer of 1996, Eldepryl's benefits when administered in combination with Sinemet were affirmed. In fact, patients taking the drug combination were shown to experience motor fluctuations 1.8 years later on average than those taking only Sinemet. Another advantage of taking Eldepryl is that there is no specific dietary restriction associated with it if taken at the 5 mg dosage. Seleginine is an easy drug to take and has further been shown to protect the dopamine-producing neurons against the toxicity of MPTP. However, selegiline has its drawbacks. Patients have been known to experience side effects such as nausea, orthostatic hypotension and insomnia.

Dopamine agonists comprise another general category of drugs. Parlodel (generic name of bromocriptine), Permax (generic name of pergolide) and Symmetrel (generic name of amantadine) are examples. Parlodel and Permax mimic the action of dopamine by interacting with dopamine receptors in a form of dopamine substitution therapy. These two drugs enter the brain directly at dopamine receptor sites and prolong the duration of Sinemet's effects. An advantage of this approach is that it is less likely to cause dyskinesias (the occurrence of abnormal involuntary movements that results from the intake of high doses of L-DOPA). This is because the actual levels of dopamine do not increase in the brain, as is the case with Sinemet. Rather, a substitute form of dopamine is being used. However, these two drugs are less effective than L-DOPA in decreasing bradykinesia and rigidity and induce side effects such as paranoia, hallucinations, confusion, nausea and vomiting.

Symmetrel is an anti-viral drug used as a dopamine-releasing therapy in combination with Sinemet. It works by allowing the presynaptic neuron to more easily release dopamine into the synapse. More recently, it has been suggested that Symmetrel acts by binding to glutamate receptors in the subthalamic nucleus to help redress the imbalance in basal ganglia activity due to a deficiency in dopamine in a synergistic manner. Symmetrel is either used alone in the first stages of PD or in combination in the later stages. However, its effectiveness is known to wear off in a third to a half of the patients taking it. Furthermore, it induces side effects such as edema, blurred vision, depression, confusion and mottled skin.

Two new drugs, after having undergone extensive clinical trials, were made available in 1997. Requip (generic name of ropinirole) and Mirapex (generic name of pramipexole) are dopamine agonists. They are selective for the dopamine D3 receptor and are selectively targeted toward the basal ganglia. Both Requip and Mirapex can be used alone or with levodopa and both show fewer side effects than other drugs (Lozano et al. 1998).

Artane and Cogentine represent yet another class of drugs. They are classified as anti-cholinergic agents and are used to restore the imbalance between dopamine and acetylcholine levels in the brain. They work to reduce the activity of acetylcholine and hence reduce the tremor and stiffness of muscle that come about as a result of having more acetylcholine than dopamine in the brain.

Until the introduction of L-DOPA, anti-cholinergic agents were the main treatments for Parkinson's disease. Now Artane and Cogentine are usually administered in combination with other medications for their therapeutic effect. While effective, these drugs can also have side effects such as blurred vision, urinary retention, dry mouth, memory loss, and constipation. Hence, they are of limited use to the older population because they can cause serious neuropsychiatric side effects.

Tasmar (generic name of tolcapone) is a drug classified as a COMT inhibitor. COMT is a peripheral enzyme that reduces levodopa to a less active form. Tasmar, which became available in February 1998, has a different action than that of the dopamine agonists, in that when COMT activity is blocked, dopamine remains in the brain for a longer period of time. Hence, when administered with levodopa, COMT inhibitors prolong the duration time of Sinem.

SUMMARY OF THE INVENTION

A method and apparatus are disclosed for treating a variety of conditions. These include treating a disorder associated with neural activity near a region of a brain. In such condition, the method includes placing an electrode to create a field near said region, creating said field with parameters selected to at least partially block neural activity within said field. For treating a tissue sensation, the method includes identifying a target area of tissue to be treated and placing an electrode to create a field near the target area, and creating the field with parameters selected to at least partially block neural activity within the target area. For treating a condition associated with neural activity of a spinal cord, the method includes placing an electrode to create a field near a nerve associated with the spinal cord, and creating the field with parameters selected to at least partially block neural activity within the nerve.

DESCRIPTION OF A PREFERRED EMBODIMENT

With reference now to the various drawing figures in which identical elements are identically numbered, preferred embodiments of the present invention will now be described.

A. Central Nervous System (CNS) Treatment

Certain disorders (e.g., epilepsy and Parkinson's disease and other motor disorders of CNS origin) are believed to be associated with hormonal imbalance.

Movement disorders associated with cerebral activity are not fully understood. However, certain disorders such as epilepsy and Parkinson's disease are believed to be associated with an imbalance of hormonal production deep within the brain.

For example, certain regions deep within the brain produce the hormones glutamate and dopamine. Glutamate enhances conductivity of the nerve cells of the brain while dopamine reduces or inhibits such conductivity.

Figure 3:
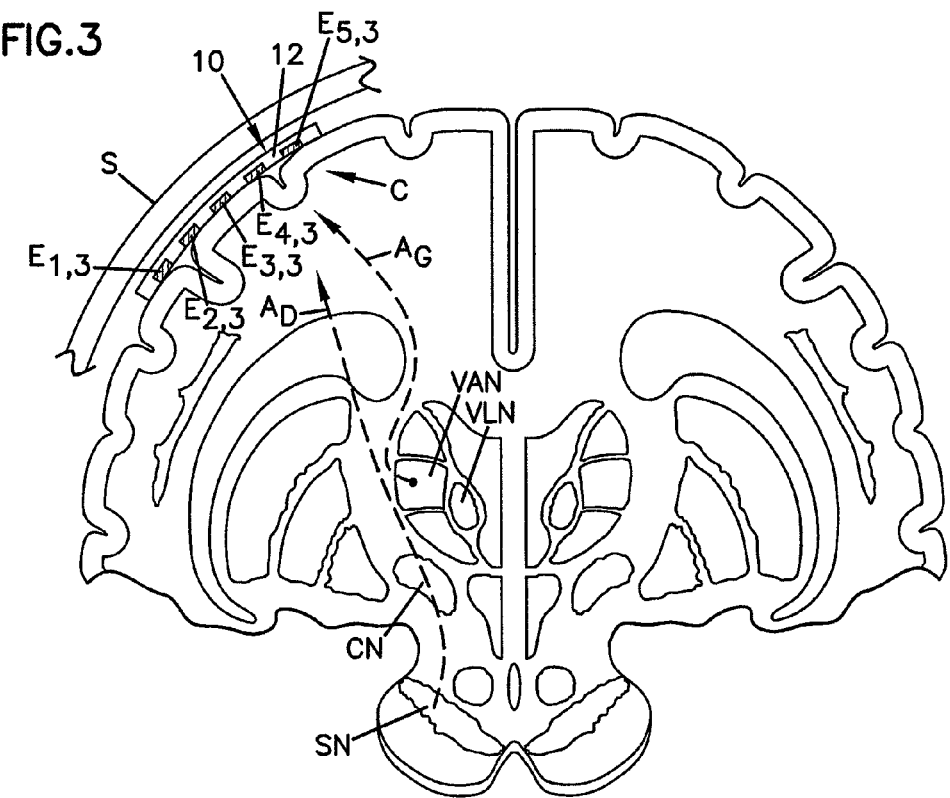
FIG. 3 is a view of a brain of a patient shown in lateral cross-section and with a patch according to the present invention residing between the skull and the surface of the patient's brain over a cortex of the patient's brain.

With reference to FIG. 3, dopamine is produced within a region of the brain known as the substantia nigra SN. Glutamate is produced in the thalamus region of the brain, which includes the ventral anterior nucleus VAN, the ventral lateral nucleus VLN and the centromedian nucleus CN. The produced hormones are projected throughout the brain including to the cortex which is the outer region of the brain near the back of the head and illustrated generally by C in FIG. 3.

The projection to the cortex C of the glutamate is believed to flow from production of glutamate in the ventral anterior nucleus VAN. Such projection is illustrated by the arrow $A_G$ in FIG. 3. The projection of dopamine to the cortex is believed to flow from the substantia nigra SN with such projection illustrated in FIG. 3 by the arrow $A_D$.

The presence of dopamine and glutamate in the cortex C alter the conductivity of the nerve cells in the cortex C. Certain motor disorders such as epilepsy and Parkinson's disease, are believed to be associated with a deficiency of dopamine production which results in excessively enhanced conductivity in the cortex since the enhancing hormone, glutatmate, is disproportionately high relative to the inhibiting conductivity hormone, dopamine.

The present invention compensates for hormonal imbalance resulting in excessive conductivity by altering the conductivity at the cortex. The conductivity of the cortex and electrical activity of the cortex controls motor functions of the patient.

The present invention is a patch electrode 10, which is placed beneath the skull of the patient between the skull S and the cortex C (FIG. 3). The patch electrode 10 includes a flexible flat substrate 12 of electrically insulating material such as silicone or the like. Exposed on one surface of the substrate 12 are a plurality of electrically conductive electrodes, which, in a preferred embodiment, are arranged in an array of rows and columns.

Figure 4:
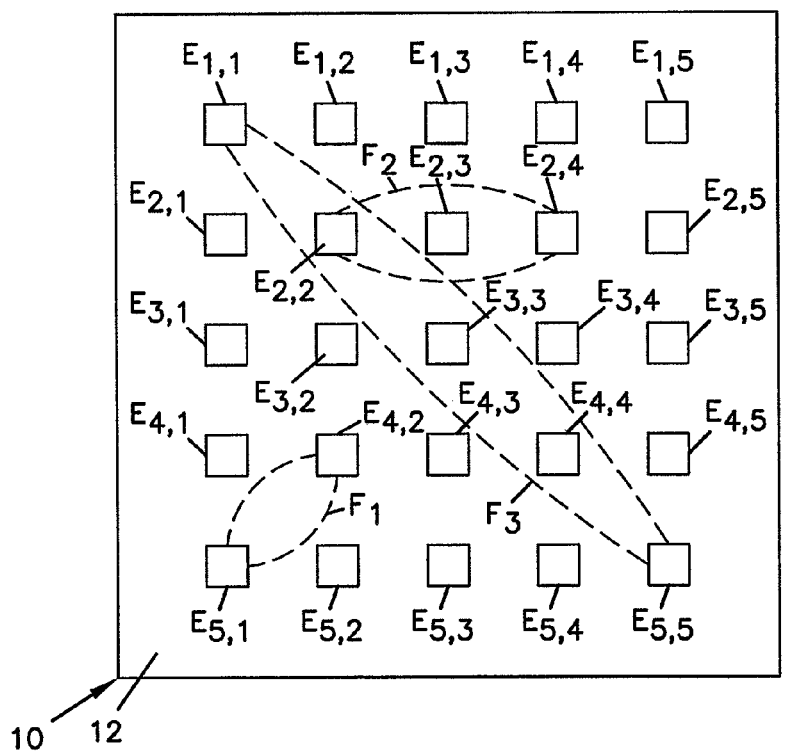
FIG. 4 is a plan view of an electrode patch according to the present invention.

In the specific examples shown in FIGS. 3 and 4, there is a first row containing electrodes $E_{1,1}$ through $E_{1,5}$. The second row contains five electrodes $E_{2,1}$ through $E_{2,5}$. The third row contains electrodes $E_{3,1}$ through $E_{3,5}$. The fourth row contains electrodes $E_{4,1}$ through $E_{4,5}$. The fifth row contains electrodes $E_{5,1}$ through $E_{5,5}$. The patch 10 is dimensioned for the array of electrodes to cover at least a portion of the cortex C of the brain and with the electrodes of the array in electrically conductive contact with the cortex C.

Figure 1:
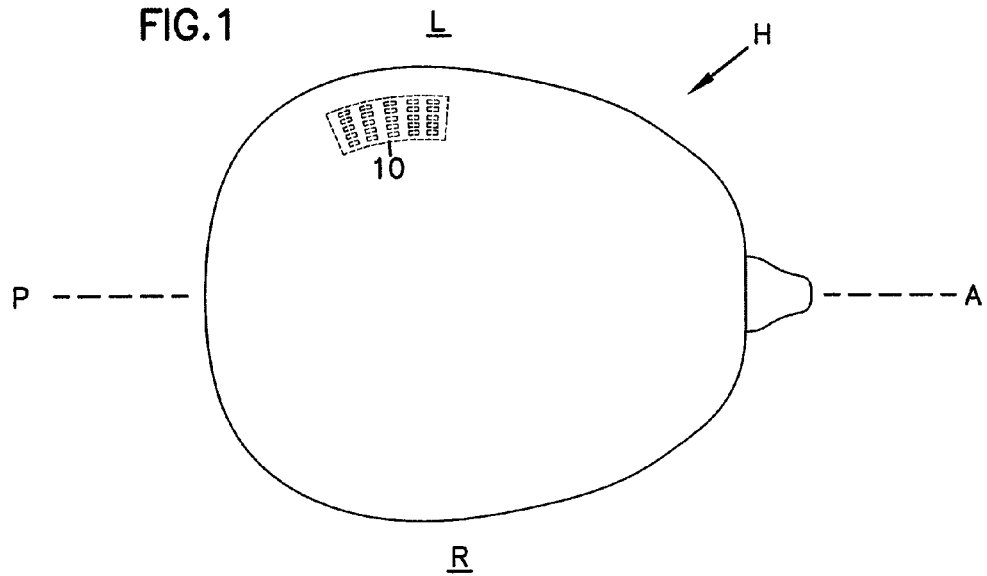
FIG. 1 is a top plan view of a patient's head and showing an electrode array according to the present invention in phantom lines positioned beneath a skull of the patient.
Figure 2:
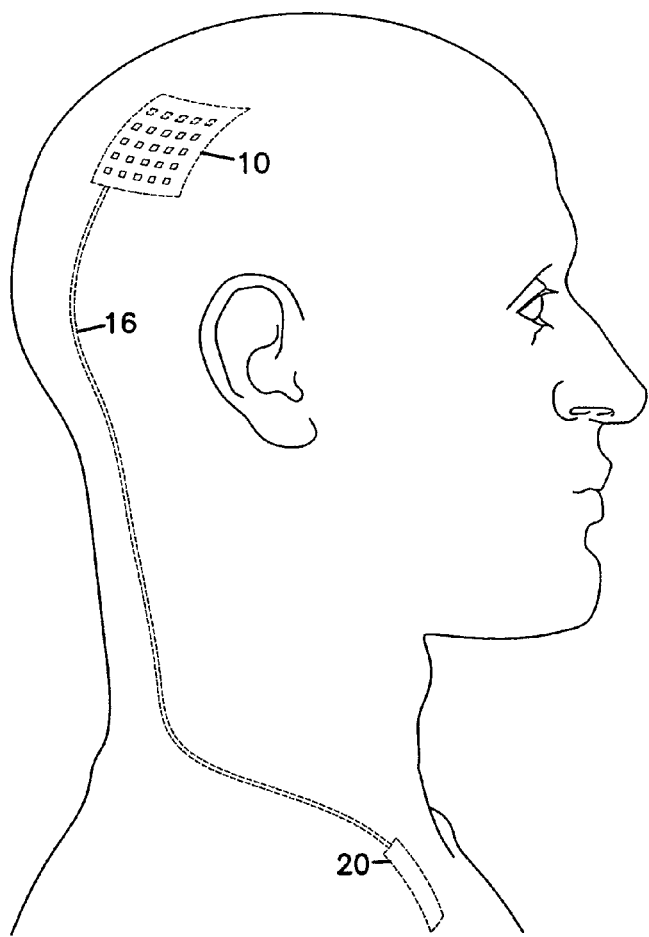
FIG. 2 is a side elevation view of a patient with an electrode patch beneath the skull of the patient and shown in phantom lines with a lead to a control unit positioned in the patient's neck.

As illustrated in FIGS. 1 and 2, the patch electrode 10 is placed over the cortex beneath the skull on either the left (FIG. 1) or right (FIG. 2) of the brain. In FIG. 1, the top of a patient's head H is shown with an anterior-posterior axis A-P separating the patients' left L and right R sides.

As shown in FIG. 2, a lead 16 from the patch electrode 10 may be tunneled between the skull S and the brain B through the base of the skull and terminated at a control unit 20 which may be positioned within the neck or implanted lower in the patient such in the shoulder or clavicle area or the like. The lead 16 is a highly flexible conductor containing individual conductors for each of the electrodes of the array of the patch 10 and encased within a highly flexible insulative material such as silicone or the like.

The controller 20 may be an implantable pulse generator (with separate power source such as either rechargeable batteries or replaceable batteries) or may be a control unit, which receives power and pacing signals from an external control unit, which transmits via radio frequency transmission to the controller 20. For the purpose of this description, the controller 20 will be treated as a completely contained controller having both logic circuits and power source. It will be appreciated that such controllers may be also programmable from external programmable sources as is known in the art for controlling implantable pulse generators for cardiac pacing.

The circuitry of the controller 20 permits energizing selective ones of the electrodes of the array in bi-polar electrode pairs. For example, electrodes $E_{5,1}$ and $E_{4,2}$ may be energized with oppositely polarized waveforms to create an electrical field $F_1$ between the electrodes $E_{5,1}$ and $E_{4,2}$. By oppositely charged waveforms it will be appreciated that electrode $E_{5,1}$ is positively charged while $E_{4,2}$ is negatively charged and $E_{5,1}$ is negatively charged while $E_{4,2}$ is positively charged. When the electrode pair $E_{5,1}$ and $E_{4,2}$ is charged to create the field $F_1$, all remaining electrodes may be inactive or otherwise charged to create more complex electrical fields.

FIG. 4 illustrates a field $F_2$ created between electrode pairs $E_{2,2}$ and $E_{2,4}$ and a field $F_3$ between electrode pairs $E_{1,1}$ and $E_{5,5}$. While multiple electrode pairs may be simultaneously charged, the controller 20 may also control the electrodes so that the waveform applied to the electrodes has a built-in delay period such that a particular electrode pair is not charged and in its delay period, while other electrode pairs are being charged. Accordingly, multiple pairs of electrodes may be charged with the waveforms of the electrode pairs being nested so that only one electrode pair is charged at any one unit of time. An example of a nested set of waveforms will be later described.

Preferably, the waveform selected is a blocking waveform to block neuronal activity. For example, the frequency of the field will have a pulse width selected for the generated field to have a frequency in excess of a 200 Hz threshold as described by Solomonow (article previously described) and, more preferably, 5,000 Hz or higher as described in Kilgore (article previously described). A 5,000 Hz signal will have a pulse width of about 100 microseconds. A representative amplitude for such signals would be 0.2 to 8 mA.

The effect of applying a blocking signal to the cortex reduces the excessive electrical activity otherwise associated with a dopamine deficiency. Further, the therapy of the present invention is localized to the area of interest, namely, the cortex region of the brain, which contributes to the symptoms of motor disorders. Other regions of the brain are not affected and no systemic drug is given to the patient.

The programming of the controller 20 may permit altering the selected individual electrodes, which form an electrode pair. Any two electrodes on the patch 10 may be formed to a pair to create a field between the pair. As a result, at time of placement of the patch 10, the patch need not be precisely placed to achieve an interruption or inhibition of electrical activity in the cortex. Instead, different permutations of coupled electrode pairs may be tested to observe patient response post-surgery.

Figure 5:
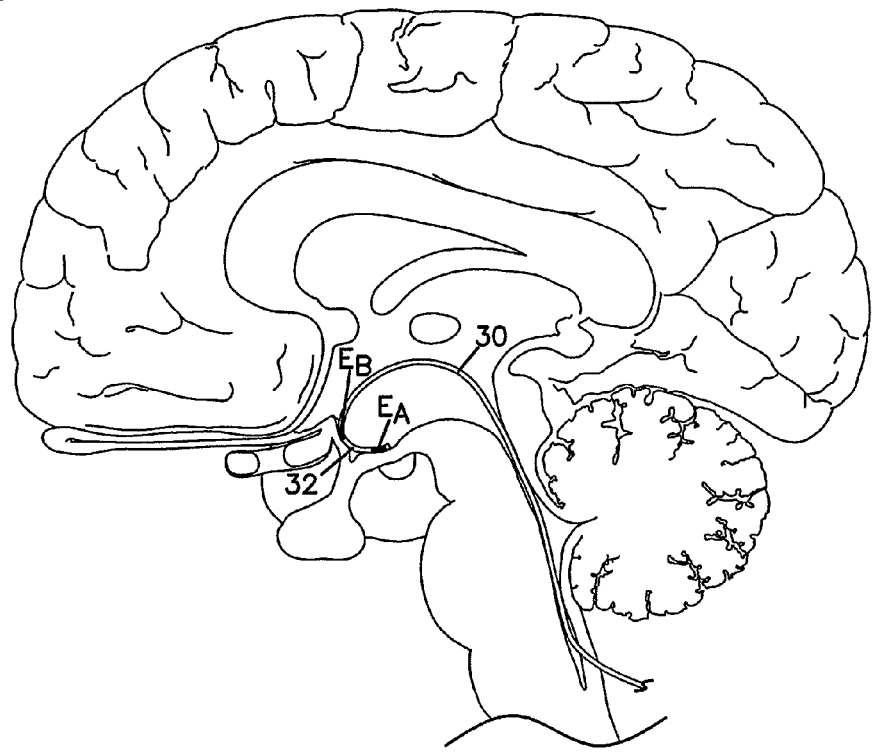
FIG. 5 is an anterior-posterior, cross-sectional view of a patient's brain showing an alternative embodiment of electrodes placed on a catheter advanced through the ventricle of the brain.

The forgoing has illustrated use of the blocking signals to compensate and down regulate cortex electrical conductivity in response to dopamine deficiency. FIG. 5 illustrates use of stimulation signals to result in localized production of dopamine. In FIG. 5, a catheter 30 is advanced into the ventricles of the brain with a distal tip 32 positioned in the region of the hypothalamus of the brain. The tip 32 includes an electrode pair $E_A$ and $E_B$, which form a bi-polar electrode pair. The electrodes are individually electrically connected to a controller (not shown but such as controller 20 previously described) for creating a desired waveform (as will be described). The controller provides the electrodes with either a stimulation signal (for example 20 Hz or any other signal less than 200 Hz) or a blocking signal as previously described. Energizing the electrodes with a stimulation signal can be tested on a particular patient to note any increase in dopamine production and result in cortex activity. Similarly, a blocking signal can be applied to note any reduction in glutamate production.

B. Peripheral Nervous System Treatment

The use of blocking signals as described may be used to alleviate pain on the surface of the skin for a wide variety of applications. For example, FIGS. 6 and 7 illustrate a patch 110 which may be placed on the skin surrounding a target area T associated with pain.

Figure 6:
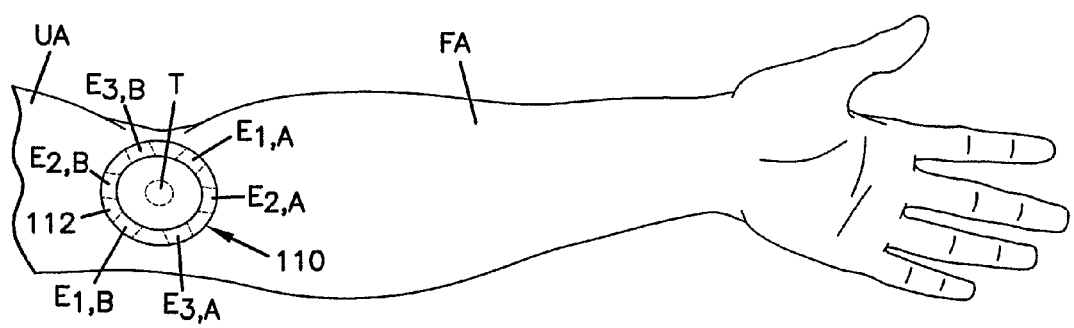
FIG. 6 is a plan view of inside surfaces of an upper arm and forearm and hand of a patient with an alternative embodiment of the present invention positioned surrounding a target area for needle insertion.
Figure 7:
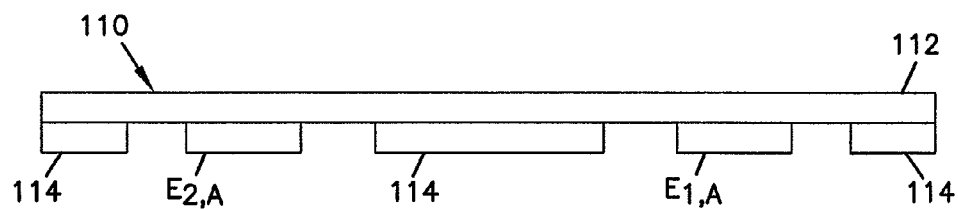
FIG. 7 is a side elevation view of a section of the electrode patch of FIG. 6.

In the particular illustration of FIG. 6, a patient's required to give blood samples frequently require a needle injection into the interior surface of the arm to insert a needle into a vein between the upper arm UA and the forearm FA. The health care technician's identification of the particular vein for puncture is identified and circled by a target area T in phantom lines in FIG. 6.

A patch 110 is a ring-shaped substrate 112 sized to surround the target area T but otherwise permits access to the target area T by a needle (not shown) for drawing blood or the like. An undersurface of the substrate 112 contains diametrically opposite electrode pairs $E_{1,A}$, $E_{1,B}$ and $E_{2,A}$, $E_{2,B}$ and $E_{3,A}$, $E_{3,B}$. The electrodes are individually electrically connected to a controller (not shown but such as controller 20 previously described) for creating a desired waveform (as will be described). Between the electrodes adhesive layers 114 are provided to secure the patch 110 in place on the patient's skin surrounding the target area T.

The individual electrode pairs are bi-polar electrode pairs, which may be provided with a blocking signal as previously described. For example, the electrode pair $E_{1,A}$, $E_{1,B}$ may be provided with a first waveform $W_1$ illustrated in FIG. 8. The electrode pair $E_{2,A}$, $E_{2,B}$ may be provided with a second waveform $W_2$ and electrode pairs $E_{3,A}$, $E_{3,B}$ may be provided with a third waveform $W_3$ in FIG. 8.

Each of the waveforms $W_1$, $W_2$ and $W_3$ are identical differing only in their timing. The waveforms are preferably blocking waveforms having a frequency in excess of a few hundred Hz threshold and more preferably having a frequency of about 5,000 Hz. With such a frequency, the waveforms have a pulse duration D of 100 microseconds. Preferably, each cycle of the waveform has a delayed period DP between the pulses with the duration of the delay period DP equal to two complete cycles (i.e., four pulse durations D or 400 microseconds). The amplitude of the pulse A may be any suitable amplitude to encourage current flow between the electrode pairs. To drive current across the skin, higher energy levels are anticipated (e.g., voltages up to about 35 volts and currents up to 25 mA).

Figure 8:
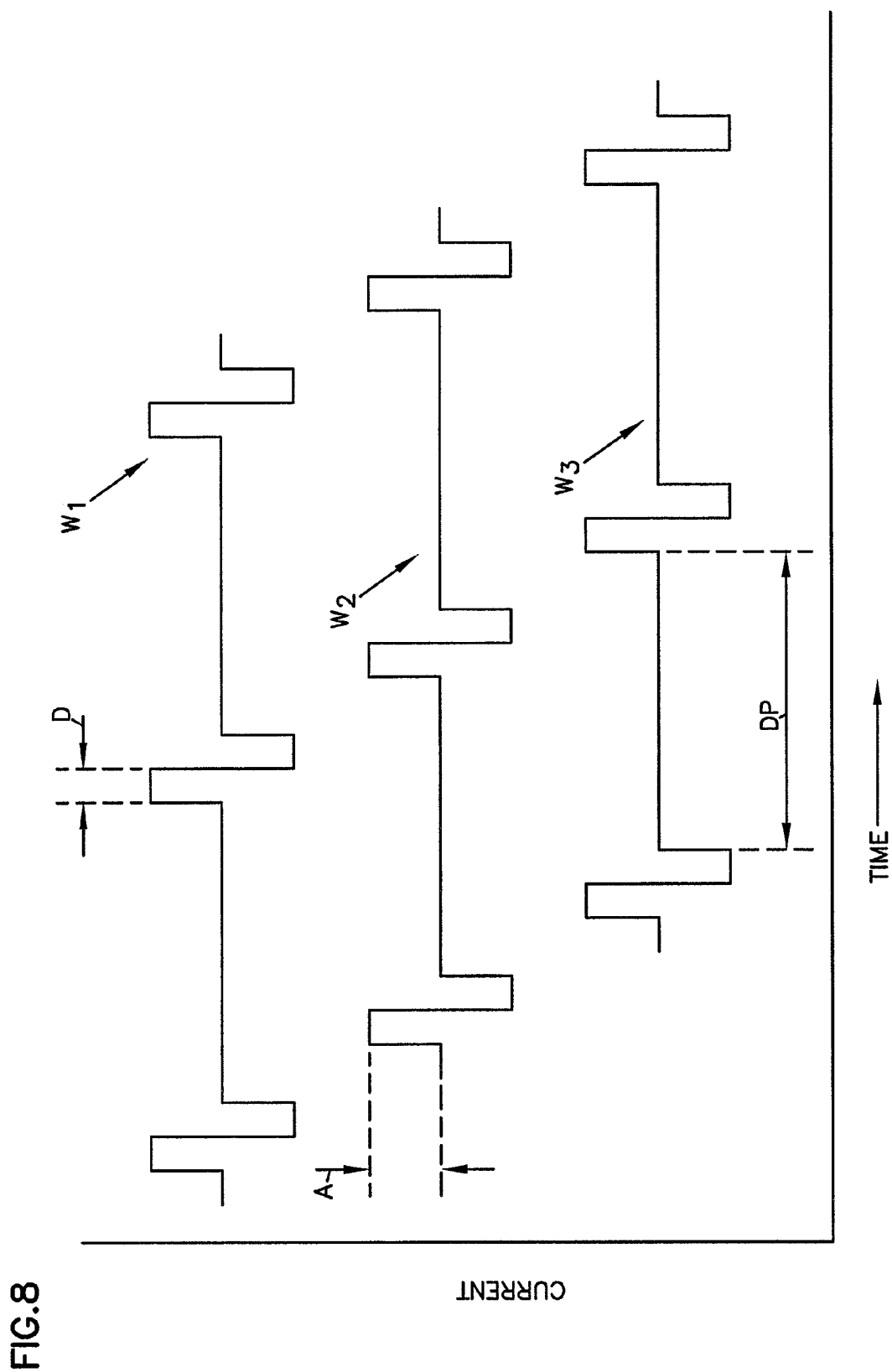
FIG. 8 is a graphical presentation of representative waveforms according to the present invention for energizing the electrodes of FIG. 6.

The waveforms are offset relative to one another so that when any one electrode pair is receiving a pulse, the other electrode pairs are inactive resulting in three nested waveforms as illustrated in FIG. 8. Such waveforms create an electrical field between the diametrically opposed electrodes of a particular pair with the field passing through the target area T to block neuronal activity within the target area. Accordingly, when the electrodes are energized with the blocking signals as described, pain is not sensed during needle insertion into the target area T.

It will be appreciated in FIG. 6 the apparatus 110 will further include electrical leads to a control unit both of which are not shown for ease of illustration.

Figure 9:
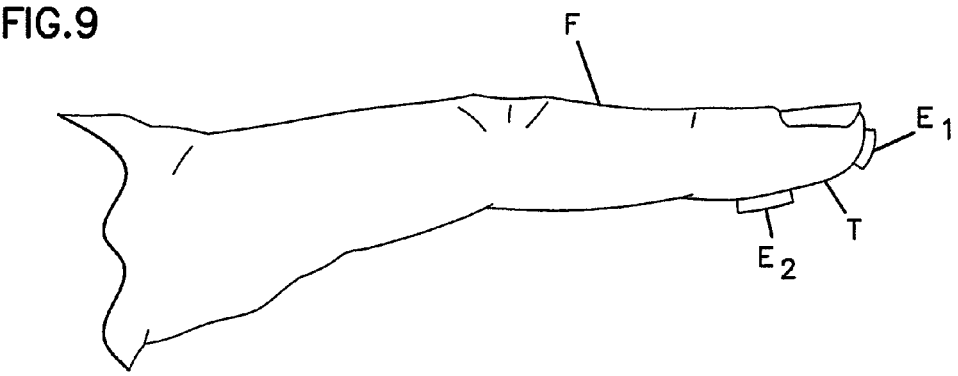
FIG. 9 is an illustration of a patient's finger showing electrodes on the opposite side of a target area at the fingertip of the patient.

FIG. 9 illustrates an alternative application where two electrodes $E_1$ $E_2$ are placed on opposite sides of a target area T near the fingertip of a patient's finger F. For ease of illustration, a substrate for the electrodes is not shown. The electrodes are individually electrically connected to a controller (not shown but such as controller 20 previously described) for creating a desired waveform. The application of FIG. 9 is particularly useful for numbing a fingertip prior to lancing the fingertip for a blood sample for periodic blood sugar tests by diabetic patients.

Figure 10:
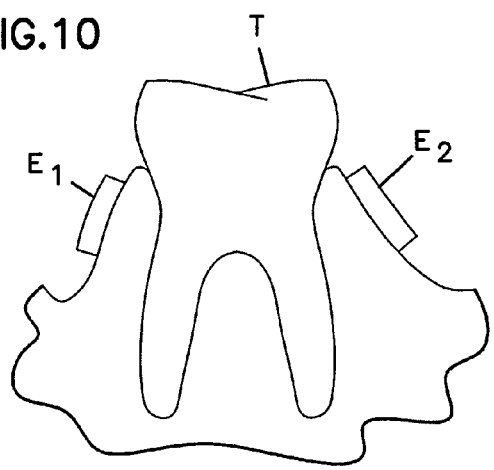
FIG. 10 illustrates electrodes on mucosal tissue on opposite sides of a tooth to apply a blocking signal.

FIG. 10 illustrates a still further embodiment where electrodes $E_1$ and $E_2$ are placed on opposite sides of the gum of the patient overlying mucosal tissue MT on opposite sides of a tooth T. Application of a blocking signal as previously described to the electrodes creates a blocking field to block nerves within the mucosal tissue for treatment of pain associated with gums or teeth or to precondition the tissue prior to injection of local anesthetics such as Novocain or Lydacain or other procedure occurring at the tissue.

C. Spinal Cord Treatment

Figure 11:
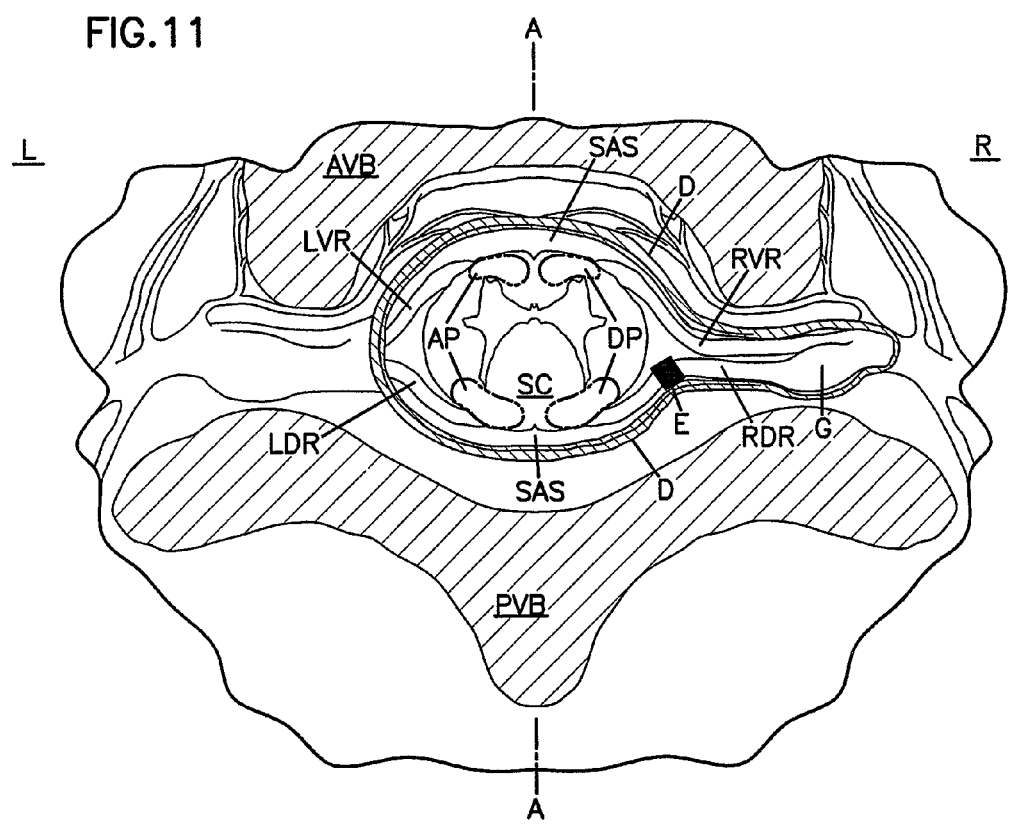
FIG. 11 is a cross-section view of a vertebral body and showing anatomical components and a blocking signal electrode on a dorsal root.
Figure 12:
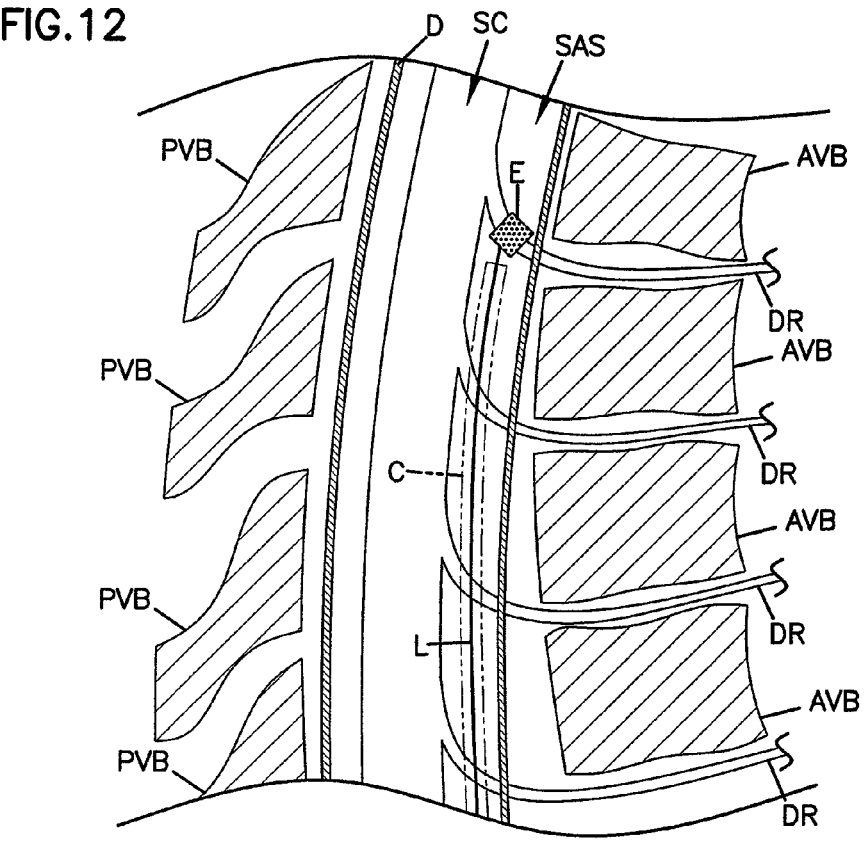
FIG. 12 is a schematic longitudinal, side-sectional showing of a segment of a spine with a catheter placement of an electrode on a dorsal root.
Figure 13:
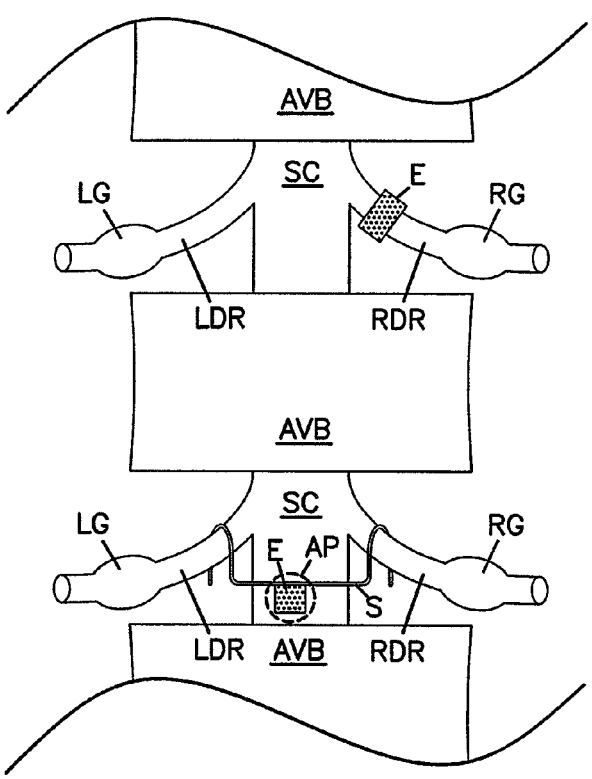
FIG. 13 is an anterior-posterior schematic representation of a segment of a spine with blocking signal electrodes shown in two positions.

FIGS. 11-13 illustrate application of the present invention to the spinal cord. By way of anatomical background, FIG. 11 shows, in cross section, a spinal cord SC position between an anterior vertebral body AVB and a posterior vertebral body PVB. The patient's anterior-posterior axis A-P is shown separating the patient's right R and left L sides.

The spinal cord SC is shown enclosed within a dural layer D with opposing surfaces of the spinal cord SC and the dural D defining a subanachroid space SAS. Extending laterally away from the spinal cord are left and right ventral roots LVR, RVR and right and left dorsal roots RDR, LDR. Also illustrated is a ganglion G. The spinal cord SC is illustrated as having identifiable areas of afferent and efferent fibers including ascending pathways AP areas and descending pathways DP areas.

According to the present invention, an electrode E is advanced either through open surgical or minimally invasive techniques into the subanachroid space SAS and positioned on a root such as the right dorsal root RDR. Application of a blocking signal to the electrode E blocks signals such as pain signals from the dorsal root the spinal cord SC. While a single monopolar electrode E is shown in FIG. 11, it will be appreciated that multiple electrodes including bipolar electrodes may be placed on the roots. For spinal treatments, such blocking signal may be as previously described and, preferably, has a frequency in excess of 3,000 Hz and more preferably about 5,000 Hz or more.

FIG. 12 is shown in vertical cross section with multiple vertebral bodies and with a spinal cord extending between the vertebral bodies. For ease of schematic illustration, the dorsal roots are shown extending between the anterior bodies. It will be appreciated that such roots extend laterally from the spinal cord.

A catheter C is shown in phantom lines for advancing an electrode to a dorsal root for placing the electrode on the dorsal root. The electrode lead extends from the electrode through implantable or external pulse generator as previously described.

FIG. 13 illustrates an electrode E (the upper electrode E in the view of FIG. 13) placed on a dorsal root either surgically or through catheter delivery as previously described. Further, FIG. 13 shows an electrode E (the lower electrode E in the view of FIG. 13) placed overlying the spinal cord over a target area AP, In the example of FIG. 13, the target area AP is an identified area of ascending pathways for application of a blocking signal to the ascending pathways for blocking transmission of neural signals to the brain. The electrode is supported on a sling S which is mounted on the left and right dorsal roots. It will be appreciated that the electrode so supported can be positioned over any area of the spinal cord to affect any desired area of ascending pathways or descending pathways. The electrodes are individually electrically connected to a controller (not shown but such as controller 20 previously described) for creating a desired waveform.

With the foregoing detailed description of the present invention, it has been shown how the objects of the invention have been attained in a preferred manner. Modifications and equivalents of disclosed concepts such as those which might readily occur to one skilled in the art, are intended to be included in the scope of the claims which are appended hereto.

What is claimed is:

1. A method of treating a disorder associated with a hormonal imbalance in a region of a brain, said method comprising:
    placing at least one pair of electrodes beneath a skull of said patient to create a field near said region; and
    altering a conduction of the cortex of the brain by creating said field with parameters selected to down-regulate neural activity to form an at least partial block of neural activity within said field, the parameters including a frequency of at least about 5,000 Hz, resulting in altering an effect of the hormonal imbalance on conductivity in said region of the brain.

2. A method according to claim 1, wherein the at least one pair of electrodes comprises a plurality of electrode pairs.

3. A method according to claim 2, wherein the plurality of electrode pairs are located on a patch electrode.

4. A method according to claim 2, wherein creating said field comprises energizing a first electrode of the at least one pair of electrodes with a waveform and energizing a second electrode of the at least one pair of electrodes with an oppositely polarized waveform.

5. A method according to claim 2, wherein creating said field comprises energizing each of the electrode pairs of the plurality of electrode pairs by energizing a first electrode of the at least one pair of electrodes with a waveform and energizing a second electrode of the at least one pair of electrodes with an oppositely polarized waveform.

6. A method according to claim 5, wherein each electrode pair is energized during a delay period of the other electrode pairs.

7. A method according to claim 1, wherein creating said field comprises energizing a first electrode of the at least one pair of electrodes with a waveform and energizing a second electrode of the at least one pair of electrodes with an oppositely polarized waveform.

8. A method according to claim 1, wherein the parameters selected to down-regulate neural activity to form an at least partial block of neural activity within said field comprise a current of about 0.2 to about 8 mAmp.

9. A method of claim 1, wherein the hormonal imbalance comprises a decrease in dopamine.

10. A method of claim 1, wherein the hormonal imbalance comprises an increase in the ratio of glutamate to dopamine.

11. A method of claim 1, wherein the disorder is Parkinson's disease.

12. A method of claim 1, wherein the disorder is epilepsy.

13. An apparatus for treating a disorder associated with a hormonal imbalance in a region of a brain, said apparatus comprising:
    at least one pair of electrodes for creating a field near said region, said electrode adapted to be placed beneath a skull of said patient near said region; and
    a controller configured to create said field at said electrode, wherein said field is effective to alter a conduction of the cortex of the brain, resulting in altering an effect of the hormonal imbalance on conductivity in said region of the brain, said controller configured with parameters selected to down-regulate neural activity to form an at least partial block within said field, the parameters including a frequency of at least about 5,000 Hz.

14. An apparatus according to claim 13, wherein the at least one pair of electrodes comprises a plurality of electrode pairs.

15. An apparatus according to claim 14, wherein the plurality of electrode pairs are located on a patch electrode.

16. A apparatus according to claim 14, wherein said controller is configured to create said field by energizing each of the electrode pairs of the plurality of electrode pairs by energizing a first electrode of the at least one pair of electrodes with a waveform and energizing a second electrode of the at least one pair of electrodes with an oppositely polarized waveform.

17. An apparatus according to claim 16, wherein said controller is configured to energize each electrode pair during a delay period of the other electrode pairs.

18. An apparatus to according to claim 13, wherein said controller is configured to create said field by energizing a first electrode of the at least one pair of electrodes with a waveform and energizing a second electrode of the at least one pair of electrodes with an oppositely polarized waveform.

19. An apparatus according to claim 13, wherein the parameters selected to down-regulate neural activity to form an at least partial block of neural activity within said field comprise a current of about 0.2 to about 8 mAmp.

20. An apparatus of claim 13, wherein the controller is configured to create—said field at said electrode effective to alter an effect of the hormonal imbalance—, wherein the hormonal imbalance comprises a decrease in dopamine.

21. An apparatus of claim 13, wherein the controller is configured to create said field at said electrode effective to alter an effect of the hormonal imbalance, wherein the hormonal imbalance comprises an increase in the ratio of glutamate to dopamine.

22. An apparatus of claim 13, wherein the disorder is Parkinson's disease.

23. An apparatus of claim 13, wherein the disorder is epilepsy.

* * * * *